(12) United States Patent
Ni

(10) Patent No.: US 12,097,380 B2
(45) Date of Patent: Sep. 24, 2024

(54) SHIELDING OF MAGNETIC FIELD AS A MEDICAL THERAPY

(71) Applicant: Micromed Scientia, Inc., Riviera Beach, FL (US)

(72) Inventor: Jiu Xiang Ni, San Francisco, CA (US)

(73) Assignee: MICROMED SCIENTIA, INC., Riviera Beach, FL (US)

( * ) Notice: Subject to any disclaimer, the term of this patent is extended or adjusted under 35 U.S.C. 154(b) by 85 days.

(21) Appl. No.: 17/088,509

(22) Filed: Nov. 3, 2020

(65) Prior Publication Data
US 2021/0113848 A1 Apr. 22, 2021

Related U.S. Application Data

(63) Continuation of application No. 14/093,187, filed on Nov. 29, 2013, now Pat. No. 10,843,005.

(60) Provisional application No. 61/731,385, filed on Nov. 29, 2012.

(51) Int. Cl.
*A61N 2/00* (2006.01)
*C12N 13/00* (2006.01)
*G01N 33/50* (2006.01)

(52) U.S. Cl.
CPC ............ *A61N 2/004* (2013.01); *A61N 2/002* (2013.01); *C12N 13/00* (2013.01); *G01N 33/502* (2013.01); *G01N 2800/52* (2013.01)

(58) Field of Classification Search
CPC ...... A61B 5/0046; A61B 6/107; A41D 31/26; A61N 2/004; A61N 2/002; C12N 13/00; G01N 33/502; G01N 2800/05
See application file for complete search history.

(56) References Cited

U.S. PATENT DOCUMENTS

| 220,748 | A | * | 10/1879 | Brownell ................ F24H 1/182 220/692 |
| 557,504 | A | * | 3/1896 | Grant ...................... F24H 1/182 228/139 |
| 674,394 | A | * | 5/1901 | Beck et al. .......... B23K 20/001 138/143 |
| 4,665,898 | A | | 5/1987 | Costa et al. |

(Continued)

FOREIGN PATENT DOCUMENTS

| CH | 675949 A5 | * | 11/1990 |
| CN | 1068746 A | | 2/1993 |

(Continued)

OTHER PUBLICATIONS

He et al., "Influence of Constant and Strong Magnetic Field in combination with Pingyangmycin on In-vitro Culturing of Oral and Maxillofacial Region Cancer Cells", Chinese Journal of Physical Therapy, 1995, vol. 18, No. 4, pp. 204-251.

(Continued)

*Primary Examiner* — Thaddeus B Cox
*Assistant Examiner* — Joshua Daryl D Lannu
(74) *Attorney, Agent, or Firm* — Foley & Lardner LLP

(57) ABSTRACT

Provided are methods for disrupting dipolar interactions in vivo and in vitro, as wells as treating conditions associated with abnormal cell growth, by subjecting to an artificial, stable magnetic field. Also provided are assays involving an artificial, stable magnetic field. Additionally, the exposure of an artificial, stable magnetic field may be combined with other non-magnetic therapy in treatment or assays.

5 Claims, 7 Drawing Sheets

(56) References Cited

U.S. PATENT DOCUMENTS

| | | | |
|---|---|---|---|
| 4,889,124 A | 12/1989 | Schneider | |
| 5,183,456 A | 2/1993 | Liboff et al. | |
| 6,679,827 B2 | 1/2004 | Sandstrom | |
| 7,297,100 B2 | 11/2007 | Thomas et al. | |
| 8,192,969 B2 | 6/2012 | Tofani | |
| 2001/0037063 A1* | 11/2001 | Albert | G01R 33/445 600/420 |
| 2002/0103515 A1 | 8/2002 | Davey et al. | |
| 2010/0063346 A1 | 3/2010 | Murphy et al. | |
| 2010/0125191 A1 | 5/2010 | Sahin | |
| 2012/0083005 A1 | 4/2012 | Malecki et al. | |
| 2012/0171744 A1 | 7/2012 | Souza | |
| 2014/0368061 A1* | 12/2014 | Duthilleul | A61N 1/16 307/326 |

FOREIGN PATENT DOCUMENTS

| | | | | |
|---|---|---|---|---|
| CN | 201188741 Y | * | 1/2009 | |
| JP | 2003273566 A | * | 9/2003 | |
| JP | 2007242981 A | * | 9/2007 | ........... A41D 13/008 |
| TW | 201008543 A1 | | 3/2010 | |
| WO | WO-2011/061259 A1 | | 5/2011 | |

OTHER PUBLICATIONS

Jiang, Y., "Engineering Electromagnetic Fields and Waves", Huazhong University of Science & Technology Press, 2009, pp. 322-324.

Nicoll, Assessing EMP Risks, Jun. 16, 2008, eponline.com/articles/2008/06/16/assessing-emf-risks.aspx, accessed Nov. 15, 2019 (Year: 2008.

Odditycentral "Woman Allergic to Modern Technology is Forced to Live in Faraday Cage", Nov. 22, 2012 (www.odditycentral.com/news/woman-allergic-to-modern-technology-is-forced-to-live-in-faraday-cage.html, accessed May 21, 2019 (Year: 2012).

Prato et al., "Magnetoreception in laboratory mice: sensitivity to extremely low-frequency fields exceeds 33 nT at 30 Hz", J R Soc Interface 10: 20121046; Dec. 19, 2012; pp. 1-8.

Zhang et al., Protective Effects of Invariable Magnetic Field on Oxidative Damage of Schwann Cells, Journal of Shandong University (Health Sciences), 2007, vol. 45, No. 3, pp. 229-232.

* cited by examiner

SHIELDING OF MAGNETIC FIELD AS A MEDICAL THERAPY

CROSS-REFERENCE TO RELATED APPLICATIONS

This continuation application claims priority to U.S. non-provisional patent application No. 14/093,187, filed Nov. 29, 2013, which claims priority to U.S. provisional patent application No. 61/731,385, filed on Nov. 29, 2012. The content of the prior applications are incorporated herein by reference in their entirety.

FILED OF THE INVENTION

The present invention relates to therapeutic uses and assays employing stabilization of a magnetic field, for example, by shielding from the surrounding environmental magnetic field.

BACKGROUND OF THE INVENTION

Previous studies demonstrate that targeting microtubule dynamic instability and action in cancer cells can be an important strategy to develop new anti-cancer medicines[1,2]. For instance, taxol, a potent inhibitor of human HeLa and mouse fibroblast cell replication, binds with microtubules in cancer cells, thereby blocking cell replication in G2 and M phases of cell cycle and stabilizing cytoplasmic microtubules[3,4].

It has been known that van der Waals forces play an important role in the interactions among the proteins and the whole molecular interactions in a cell. The conventional wisdom suggests that protein folding, as well as micelle formation, is driven by the aversion for water of the non-polar residues, known as van der Waals force[5-9]. Additionally, van der Waals force contributes to the formation and stability of molecular clusters[10].

Therefore, interference with or the manipulation of van der Waals forces would lead to therapeutic effects by altering dipolar molecular interactions and protein folding. While many drugs act at least in part in this manner, it would be advantageous to achieve such interference/manipulation without the use of drugs to achieve therapeutic effects. Still further, it would be advantageous to synergistically combine the non-drug induced interference/manipulation of van der Waals forces with a drug so as to achieve a greater therapeutic result.

SUMMARY OF THE INVENTION

Provided herein are methods for disrupting dipolar molecular interactions in a cell so as to interfere with or manipulate molecular interactions in the cell. In one aspect, the method of this invention comprises subjecting the cell to an artificial, stable magnetic field for a period of time sufficient to result in altered dipolar interactions between molecules in the cell so as to alter the cellular physiology. In some embodiments, the period of time is at least 18 hours, at least 24 hours, at least 36 hours, at least 48 hours, at least 60 hours, or at least 72 hours.

In one embodiment, the cell is a cancer or tumor cell undergoing rapid division, and the physiology of the cell is altered so as to reduce the rate of the division. In another embodiment, the cell is an injured cell, and the physiology of the cell is altered so as to prevent premature cell death. In some embodiments, the artificial, stable magnetic field is provided by magnetic shielding or by magnetic field stabilization, such as nuclear magnetic resonance (NMR).

In another embodiment, the invention relates to a method for reducing undesired cell proliferation in a mammal. The method entails placing the mammal in an artificial, stable magnetic field which alters the physiology of proliferative cells, thereby reducing their rate of proliferation.

In some embodiments, the mammal is subjected to an artificial, stable magnetic field for a period of time sufficient to alter the physiology of proliferative cells, such as at least 18 hours, at least 24 hours, at least 36 hours, at least 48 hours, at least 60 hours, or at least 72 hours. It is within the purview of one of ordinary skill to monitor the status of the mammal and the alteration of the physiology of proliferative cells such that the mammal is not subjected to an artificial, stabile magnetic field for such a long period of time that induces adverse effects to the mammal.

In another aspect, the invention relates to a device for mammalian therapy comprising an artificial, stabilized magnetic field. The device permits the mammal to experience a localized artificial, stabilized magnetic field for a therapeutically effective time.

In some embodiments, the device is stationary. In other embodiments, the device is portable. In one embodiment, the device permits the entire body of the mammal to experience the artificial, stabilized magnetic field. Alternatively, the device permits a portion of the mammalian body to experience the artificial, stabilized magnetic field. Preferably, a portable device is attached to or implanted in at least a portion of the mammalian body such that the portion of the mammalian body is subjected to the artificial, stabilized magnetic field.

The therapeutically effective time can be determined by one of ordinary skill in the art by monitoring the status of the mammal and the therapeutic effects. For example, the therapeutically effective time is at least 18 hours, at least 24 hours, at least 36 hours, at least 48 hours, at least 60 hours, or at least 72 hours. Preferably, the period of time is not so long that induces adverse effects to the mammal.

In yet another aspect, the invention relates to an assay for ascertaining the optimal condition of an artificial magnetic field therapy to maximize the therapeutic results for pathological cell growth. The method comprises the following steps:
  (a) isolating pathological cells from a mammal for in vitro culturing;
  (b) subjecting cell culture(s) of step (a) to a plurality of artificial magnetic fields wherein each of said artificial magnetic fields is maintained under different conditions from said other artificial magnetic fields;
  (c) comparing the growth of cell cultures in each of said artificial magnetic fields;
  (d) optionally repeating steps (a) through (c); and
  (e) determining the optimal condition of said artificial magnetic field based on the results of steps (a) through (d).

Preferably, the condition of an artificial magnetic field therapy is optimized such that the adverse effects associated with the therapy are minimized.

In a related aspect, the invention relates to a method for developing an in vivo personalized treatment. The method comprises:
  (a) conducting an in vitro assay for ascertaining the optimal condition of an artificial magnetic field therapy to maximize the therapeutic results for pathological cell growth, wherein the assay comprises:

(i) isolating pathological cells from a mammal for in vitro culturing;
(ii) subjecting cell culture(s) of step (i) to a plurality of artificial magnetic fields wherein each of said artificial magnetic fields is maintained under different conditions from said other artificial magnetic fields;
(iii) comparing the growth of cell cultures in each of said artificial magnetic fields;
(iv) optionally repeating steps (i) through (iii); and
(v) determining the optimal condition of said artificial magnetic field based on the results of steps (i) through (iv);
(b) correlating the optimal condition based on the in vitro assay and the condition of the in vivo treatment.

In another related aspect, the invention relates to a method for evaluating the therapeutic effect of a non-magnetic treatment for reducing undesired cell proliferation in a mammal. The method comprises:
(a) administering said non-magnetic treatment to said mammal;
(b) placing said mammal in an artificial, stable magnetic field which alters the physiology of proliferative cells before, during, or after administration of said non-magnetic treatment;
(c) comparing the growth of undesired cells before step (a) with the growth of undesired cells after step (b) to select the non-magnetic treatment that results in reduced growth of undesired cells after step (b).

In some embodiments, the non-magnetic treatment is chemotherapy, radiation therapy, thermotherapy, and monoclonal antibody therapy. In other embodiments, the undesired cell proliferation is reduced by at least 10%, at least 20%, at least 30%, at least 40%, at least 50%, at least 60%, at least 70%, at least 80%, at least 90%, or about 100%, following the treatment, in comparison to before the treatment.

In yet another aspect, the invention relates to an in vitro assay for an anti-tumor agent. The method comprises:
(a) isolating pathological cells from a mammal for in vitro culturing;
(b) culturing cell culture(s) of step (a) in the presence of said anti-tumor agent under the condition of being subjected to an artificial, stable magnetic field and under the condition of being free of said magnetic field;
(c) comparing the growth of cell cultures under each condition;
(d) selecting the anti-tumor agent which causes more cell death under the condition of being subjected to said magnetic field than under the condition of being free of said magnetic field.

In a further aspect, the invention relates to a combined therapy for treating a patient in need thereof. The method comprises:
(a) administering one or more anti-tumor agents to a patient; and
(b) subjecting the patient to an artificial, stable magnetic field which alters the physiology of proliferative cells, thereby reducing their rate of proliferation, before, after or during the treatment of the anti-tumor agent.

In some embodiments, the anti-tumor agent is selected from the group consisting of a chemotherapy, a radiation therapy, a thermotherapy, and a monoclonal antibody therapy. In other embodiments, the undesirable side effect of or resistance to the anti-tumor agent was reduced due to reduced dosage of the anti-tumor agent and/or enhanced efficacy of the anti-tumor agent following exposure to the artificial, stable magnetic field in the combined therapy. In yet other embodiments, the patient has developed resistance to one or more anti-tumor agents.

In a related aspect, the invention relates to a method for determining a reduced effective dose of an anti-tumor agent. The method comprises:
(a) isolating pathological cells from a mammal for in vitro culturing;
(b) culturing cell culture(s) of step (a) in the presence of said anti-tumor agent at various doses under the condition of being subjected to an artificial, stable magnetic field and under the condition of being free of said magnetic field;
(c) comparing the growth of cell cultures treated with various doses of said anti-tumor agent under each condition;
(d) determining a dose of said anti-tumor agent under the condition of being subjected to an artificial, stable magnetic field, which dose achieves the same reduction in cell growth but is lower than the dose under the condition of being free of said magnetic field.

In some embodiments, the anti-tumor agent is selected from the group consisting of a chemotherapy, a radiation therapy, a thermotherapy, and a monoclonal antibody therapy.

In another aspect, the invention relates to a method for inhibiting tumor metastasis in a mammal. The method comprises placing the mammal in an artificial, stable magnetic field for a period of time sufficient to alter the physiology of cells undergoing undesired proliferation at a secondary site that is different from the primary site of the mammal, thereby reducing the rate of undesired cell proliferation at the secondary site. Preferably, a biopsy is conducted after or during exposure of the mammal to the artificial, stable magnetic field.

The period of time can be determined by one of ordinary skill in the art by monitoring the status of the mammal and the alteration of the physiology of the cells at the secondary site. For example, the period of time is at least 18 hours, at least 24 hours, at least 36 hours, at least 48 hours, at least 60 hours, or at least 72 hours. Preferably, the period of time is not so long that induces adverse effects to the mammal.

DETAILED DESCRIPTION OF THE PREFERRED EMBODIMENTS

Figure 1:
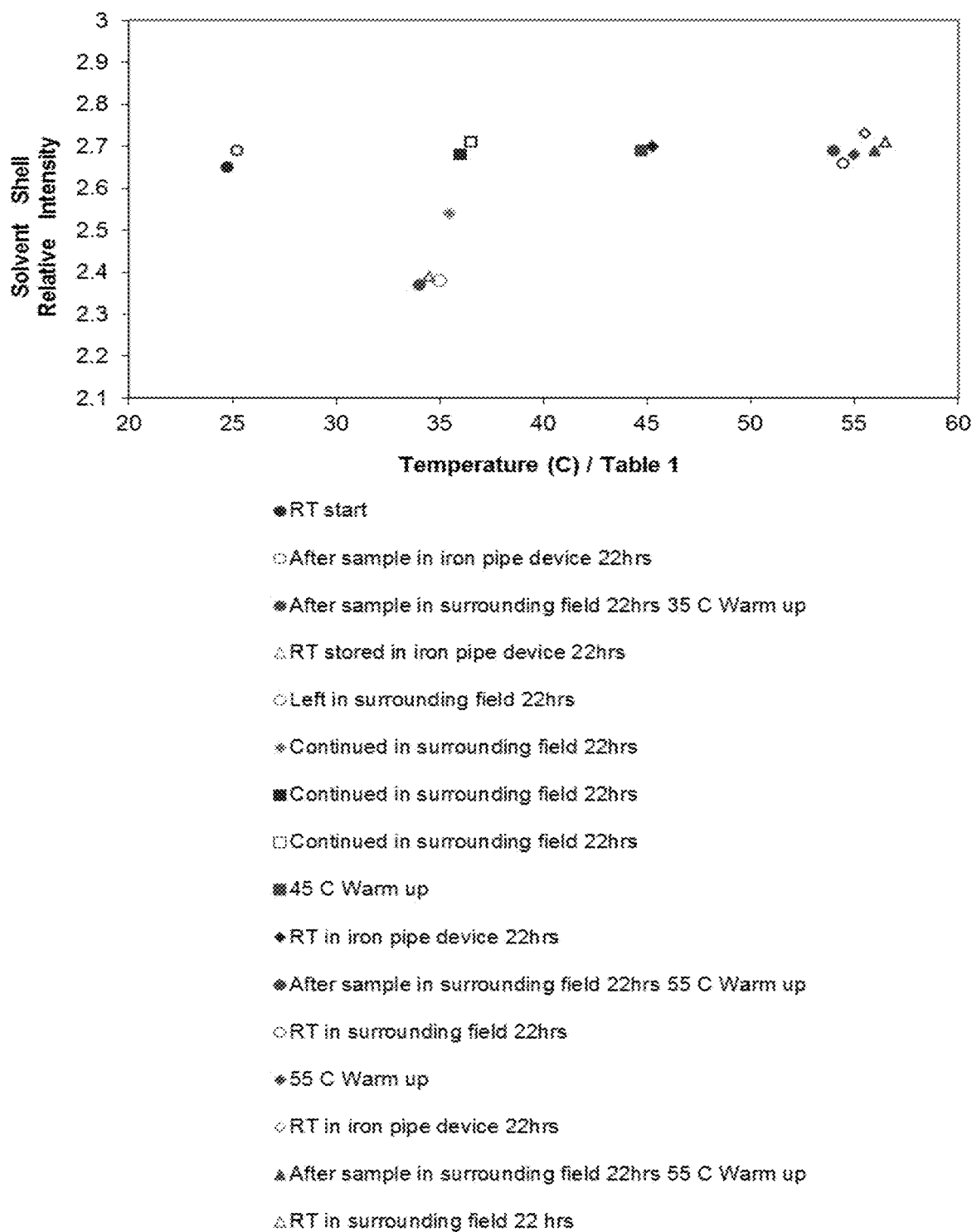
FIG. 1 demonstrates the results of surrounding magnetic field effect study and summarizes the relative NOE measurements from magnetic field shielded sample. The plot is for the solvent shell relative NOE intensity vs. temperature. In this study, the solvent was 50% DMSO-50% DMSO-d6, the toluene concentration was 0.8 M, and water concentration was 0.10 M.

It is to be understood that this invention is not limited to particular embodiments described, as such may vary. It is also to be understood that the terminology used herein is for the purpose of describing particular aspects and embodiments only, and is not intended to be limiting the scope of this invention.

It must be noted that as used herein and in the appended claims, the singular forms "a", "an", and "the" include plural referents unless the context clearly dictates otherwise.

Definitions

Unless defined otherwise, all technical and scientific terms used herein have the same meaning as commonly understood by one of ordinary skill in the art to which this invention belongs. As used herein, the following terms have the following meanings.

The term "about" when used before a numerical designation, e.g., temperature, time, amount, and concentration, including ranges, indicates approximations which may vary by (+) or (−) 10%, 5% or 1%.

As used herein, the term "therapeutically effective time" refers to the period of time that is sufficient to effect treatment, as defined herein, when a subject in need of is subjected to such a treatment. The therapeutically effective time will vary depending upon the subject and condition being treated, the weight and age of the subject, the severity of the condition, all of which can be determined readily by one of ordinary skill in the art.

As used herein, the term "treatment" or "treating" means improvement of a certain undesired condition in a subject or a patient, including:

preventing or protecting against the disease or condition, that is, causing the clinical symptoms not to develop, for example, in a subject at risk of suffering from such a disease or condition, thereby substantially averting onset of the disease or condition;

inhibiting the disease or condition, that is, arresting or suppressing the development of clinical symptoms; and/or relieving the disease or condition, that is, causing the regression of clinical symptoms.

As used herein, the term a "patient" or a "subject" refers to mammals and includes humans and non-human primate mammals.

Introduction

The inventors of the present application unexpectedly discovered that environmental magnetic field affects molecular dipole interaction in solutions. Furthermore, the inventors discovered that shielding of the environmental magnetic field surprisingly initiates the re-orientation of magnetic dipoles and changes the force of dipolar molecular interaction, thereby impacting the physiology and other biology aspects of living cells.

Therapy Using Artificial, Stable Magnetic Field

In one aspect, the invention relates to a method for disrupting dipolar molecular interactions in a cell. The method comprises subjecting the cell to an artificial, stable magnetic field for a period of time sufficient to result in altered dipolar interactions between molecules in the cell so as to alter the cellular physiology. In some embodiments, the period of time is at least 18 hours, at least 24 hours, at least 36 hours, at least 48 hours, at least 60 hours, or at least 72 hours.

In some embodiments, the cell is a cell undergoing undesired cell proliferation or rapid division, such as a cancer cell. The rate of cell proliferation or division is reduced when the cell is subjected to an artificial, stable magnetic field. In one embodiment, the artificial, stable magnetic field is provided by shielding the cell from environmental magnetic field. The main source of the environmental magnetic field is the earth's geomagnetic field, while other sources can be power lines, electric appliances, etc. The environmental magnetic field is constantly changing. Shielding the cell by certain metal materials provide an artificial, stable magnetic field for the cell. Alternatively, the artificial, stable magnetic field is provided by magnetic field stabilization, such as NMR.

In other embodiments, the cell is an injured cell, and the exposure of the injured cell to an artificial, stable magnetic field has an impact on cell apoptosis and prolongs the cell survival. For example, cell death is often preceded by protein aggregation within the cell. Heat shock proteins are generated intracellular to counter such aggregation. However, if the cell is so injured, protein aggregation still proceeds and cell death results. In the present case, the methods of this invention inhibit protein aggregation thereby prolonging cell life.

It is within the purview of one of ordinary skill in the art to determine the period of time to expose the cell to an artificial, stable magnetic field by monitoring the cell growth. Preferably, the period of time is sufficient to result in altered dipolar interactions between molecules in the cell so as to alter the cellular physiology. More preferably, the period of time is adjusted to minimize any adverse effect on the cell.

The invention is particularly useful for inhibiting tumor metastasis in a mammal. Tumor metastasis is the spread of tumor from one organ or body part (primary site) to another non-adjacent organ or body part (secondary site)[11, 12]. The method of the present invention comprises placing the mammal in an artificial, stable magnetic field for a period of time sufficient to alter the physiology of cells undergoing undesired proliferation at a secondary site that is different from the primary site of the mammal, thereby reducing the rate of undesired cell proliferation at the secondary site.

The period of time can be determined by one of ordinary skill in the art by monitoring the status of the mammal and the alteration of the physiology of the cells at the secondary site. For example, the period of time is at least 18 hours, at least 24 hours, at least 36 hours, at least 48 hours, at least 60 hours, or at least 72 hours. Preferably, the period of time is not so long that induces adverse effects to the mammal.

Therapeutic Device for Artificial, Stable Magnetic Field

This invention also encompasses a device for mammalian therapy. The device comprising an artificial, stabilized magnetic field permits the mammal to experience the artificial stabilized magnetic field for a therapeutically effective time.

In one embodiment, the device is stationary. For example, the device may be a compartment or a room composed of certain materials that shield magnetic field. The entire body of a mammal, or one or more mammals, can be enclosed in the compartment or room for a therapeutically effective time such that the mammal(s) is shielded from the environmental magnetic field for a contiguous period of time.

In another embodiment, the device is portable. For example, the device may be a container, a body wrap, a jumper suit, a glove, a sock, etc. that permits the entire body or a portion of the body of the mammal to experience the artificial, stabilized magnetic field. Preferably, a portable device is attached to or implanted into at least a portion of the mammalian body such that the portion of the mammalian body is subjected to the artificial, stabilized magnetic field for an extended period of time.

The therapeutically effective time can be determined by one of ordinary skill in the art by monitoring the status of the mammal and the therapeutic effects. For example, the therapeutically effective time is at least 18 hours, at least 24 hours, at least 36 hours, at least 48 hours, at least 60 hours, or at least 72 hours. Preferably, the period of time is not so long that induces adverse effects to the mammal.

Assay Using Artificial, Stable Magnetic Field

This invention also relates to an in vitro assay for ascertaining the optimal condition of an artificial magnetic field therapy to maximize the therapeutic results for pathological cell growth. The method comprises the following steps:
(a) isolating pathological cells from a mammal for in vitro culturing;
(b) subjecting cell culture(s) of step (a) to a plurality of artificial magnetic fields wherein each of said artificial magnetic fields is maintained under different conditions from said other artificial magnetic fields;
(c) comparing the growth of cell cultures in each of said artificial magnetic fields;
(d) optionally repeating steps (a) through (c); and
(e) determining the optimal condition of said artificial magnetic field based on the results of steps (a) through (d).

Preferably, the condition of an artificial magnetic field therapy is optimized such that the adverse effects associated with the therapy are minimized.

Different target cells respond to different treatment conditions. The treatment condition can be optimized for a particular pathological cell type. The assay is developed to optimize the treatment condition by comparing the in vitro growth of a plurality of cell cultures treated with various conditions.

Personalized Treatment Using Artificial, Stable Magnetic Field

In a related aspect, the invention relates to a method for developing an in vivo personalized treatment. The method comprises:
(a) conducting an in vitro assay for ascertaining the optimal condition of an artificial magnetic field therapy to maximize the therapeutic results for pathological cell growth, wherein the assay comprises:
  (i) isolating pathological cells from a mammal for in vitro culturing;
  (ii) subjecting cell culture(s) of step (i) to a plurality of artificial magnetic fields wherein each of said artificial magnetic fields is maintained under different conditions from said other artificial magnetic fields;
  (iii) comparing the growth of cell cultures in each of said artificial magnetic fields;
  (iv) optionally repeating steps (i) through (iii); and
  (v) determining the optimal condition of said artificial magnetic field based on the results of steps (i) through (iv);
(b) correlating the optimal condition based on the in vitro assay and the condition of the in vivo treatment.

The therapeutic effects are greatly enhanced and the safety of the in vivo treatment is improved when the treatment condition is optimized for a particular pathological cell type and personalized for the particular subject. This is because different subjects and different cells respond differently to various treatment conditions. The present invention provides method for developing an in vivo personalized treatment using an artificial, stable magnetic field by correlating the in vitro cell growth condition with an in vivo treatment condition.

Therapy in Combination with Non-Magnetic Treatment

In another related aspect, the invention relates to a method for evaluating the therapeutic effect of a non-magnetic treatment for reducing undesired cell proliferation in a mammal. The method comprises:
(a) administering said non-magnetic treatment to said mammal;
(b) placing said mammal in an artificial, stable magnetic field which alters the physiology of proliferative cells before, during, or after administration of said non-magnetic treatment;
(c) comparing the growth of undesired cells before step (a) with the growth of undesired cells after step (b) to select the non-magnetic treatment that results in reduced growth of undesired cells after step (b).

The exposure to an artificial, stable magnetic field can be used alone or in combination with other therapies that do not involve magnetic treatment, thereby enhancing the therapeutic effects of the non-magnetic treatment. In some embodiments, the non-magnetic treatment is chemotherapy, radiation therapy, thermotherapy, and monoclonal antibody therapy.

By the same token, the invention is directed an in vitro assay for an anti-tumor agent. The method comprises:
(a) isolating pathological cells from a mammal for in vitro culturing;
(b) culturing cell culture(s) of step (a) in the presence of said anti-tumor agent under the condition of being subjected to an artificial, stable magnetic field and under the condition of being free of said magnetic field;

(c) comparing the growth of cell cultures under each condition;
(d) selecting the anti-tumor agent which causes more cell death under the condition of being subjected to said magnetic field than under the condition of being free of said magnetic field.

In a further aspect, the invention relates to a combined therapy for treating a patient in need thereof. The method comprises:
(a) administering one or more anti-tumor agents to a patient; and
(b) subjecting the patient to an artificial, stable magnetic field which alters the physiology of proliferative cells, thereby reducing their rate of proliferation, before, after or during the treatment of the anti-tumor agent.

In some embodiments, the anti-tumor agent is selected from the group consisting of a chemotherapy, a radiation therapy, a thermotherapy, and a monoclonal antibody therapy. In other embodiments, the undesirable side effect of or resistance to the anti-tumor agent was reduced due to reduced dosage of the anti-tumor agent and/or enhanced efficacy of the anti-tumor agent following exposure to the artificial, stable magnetic field in the combined therapy. In yet other embodiments, the patient has developed resistance to one or more anti-tumor agents.

The inventor of the present application unexpectedly discovered that exposure to an artificial, stable magnetic field enhances the efficacy of a conventional anti-tumor agent, and that an artificial, stable magnetic field has an effect on the cell growth of cancer cells that are resistant to a conventional anti-tumor agent. This is significant for a combined therapy because the dosage of the conventional anti-tumor agent can be reduced, thereby reducing the possibility of developing resistance to the anti-tumor agent and/or eliminating other undesirable side effects associated with the anti-tumor agent.

In a related aspect, the invention relates to a method for determining a reduced effective dose of an anti-tumor agent. The method comprises:
(a) isolating pathological cells from a mammal for in vitro culturing;
(b) culturing cell culture(s) of step (a) in the presence of said anti-tumor agent at various doses under the condition of being subjected to an artificial, stable magnetic field and under the condition of being free of said magnetic field;
(c) comparing the growth of cell cultures treated with various doses of said anti-tumor agent under each condition;
(d) determining a dose of said anti-tumor agent under the condition of being subjected to an artificial, stable magnetic field which dose achieves the same reduction in cell growth but is lower than the dose under the condition of being free of said magnetic field.

In some embodiments, the anti-tumor agent is selected from the group consisting of a chemotherapy, a radiation therapy, a thermotherapy, and a monoclonal antibody therapy.

As it is well known in the art, many non-magnetic therapies have adverse effects. The invention provides an approach, when used in combination with other therapies, not only enhances the therapeutic effects of other therapies, but also reduces the dosage of other therapies while maintaining the same level of therapeutic effects. Preferably, the invention provides an assay for selecting an effective anti-tumor agent. In another preferred embodiment, the invention provides a method for determining a reduced effective dosage of an anti-tumor agent, thereby reducing the undesirable side effect of the anti-tumor agent.

This invention is further defined by reference to the following example(s). It will be apparent to those skilled in the art that many modifications, both to materials and methods, may be practiced without departing from the scope of the current invention.

EXAMPLE 1

Effect of Environmental Magnetic Field on Molecular Dipole Interaction in Solutions This example demonstrates the effect of environmental magnetic field on molecular dipole interaction in solutions.

1.1 Nuclear Overhauser Effect (NOE) Study

Materials and Device: A galvanized iron pipe device was used to shield the studied "solution" in the NMR tube from the environmental magnetic field. The device was composed from an 18 inch long 1" O.D. galvanized iron conduit, a 18 inch long ¾" O.D. galvanized iron conduit and a 16 inch long ⅜" O.D. copper pipe and was capped on both ends with threaded, galvanized, cast iron pipe caps.

Toluene (99.7%, Fisher Scientific), p-Xylene (99+%, Aldrich), 4-tert-Butylpyridine (99%), Aldrich) and DMSO (99.9%, Aldrich), distilled under Argon before use and dried on molecule sieve (4 A). DMSO-d6 (D 99.9%) was obtained from Cambridge Isotope Laboratories, Inc. HPLC, UV spectrophotometry grade $H_2O$ (Mallinckrodt) was used in the study.

A Toluene sample in 50% DMSO-50% DMSO-d6 with Toluene concentration of 0.8 M and water content of 0.10 M was used in this study. The sample was subjected to three "decrease and recovery" activation temperature stages (35° C., 55° C. and 75° C.) and an "equilibrium temperature" of 85° C.-95° C.

NMR Study: 0.75 ml 50% DMSO-50% DMSO-d6 solvent and 64.1 µl (for 0.8M Conc. Study) Toluene were added to Argon flashed dry JYoung NMR tube. The NOE intensity changes of DMSO solvent shell were studied with 1D selective NOESY (NOESY1D) NMR experiment (excitation of ortho protons on Toluene at 7.182 ppm) provided by Bruker Topspin 1.3 software and carried out on a Bruker Avance 400 MHz spectrometer. All experiments were performed at 298.0° K (25° C.). The parameters of "1D Selective NOESY" (NOESY1D) NMR experiments in this study were based on the recommendation of "Bruker NMR Experiment Guide": Recycle delay D1[s]=8, Number of dummy scans DS=8, Acquisition time AQ[s]=3.9584243 and Mixing time D8[s]=0.750. NOE was verified by decreasing D8[s] from 0.750 to 0.500, 0.300 and then to 0.200, the weakening of intensities of NOE signals was observed, and D1[s] was also examined by changing from 3, 4, 6, 8, 16 seconds to 36 seconds, it did not affect the results of DMSO solvent shell NOE intensity "decrease and recovery" observed based on NOE measurements. The measurement and data process of 1H T1 and $(T1)_M$ relaxation followed the method (inverse-recovery) and procedure provided also by Bruker Topsin 1.3 software and "Bruker NMR Experiment Guide". The T1 relaxation times of protons on Toluene methyl group and protons ortho to methyl group on phenyl ring were monitored during the study. They remained constant with average deviation less than 2%. Thus, NOE between protons on methyl group and protons ortho to methyl group on phenyl ring could be used as an internal standard (Unit) to estimate the change of solvent shell NOE and characterize the studied system.

Specifically, after the sample was warmed up in 35° C. water bath for 6 minutes, cooled down at room temperature for one hour and then its solvent shell relative NOE intensity was recorded as usual, when the sample was ejected from the NMR magnet, it was immediately inserted into the iron pipe device and left in the device for 22 hours. Subsequently, the sample was taken out of the iron pipe device to continue the NMR study.

Results: The prepared samples were left at room temperature and exposed to environmental magnetic field overnight and then measured for the solvent shell relative NOE intensity. The original intensities were 2.65 and 2.71. The intensity was 2.69 after being stored in the iron pipe device to shield from environmental magnetic field for 22 hours. Thus, shielding from the environmental magnetic field at room temperature did not significantly change the solvent shell relative NOE intensity of the samples.

Following the measurement of initial intensity, the samples were exposed to environmental magnetic field for another 22 hours and then warmed up in 35° C. water bath for 6 minutes, followed by cooling down at room temperature for one hour. The solvent shell relative NOE intensities turned out to be 2.37 and 2.36. Subsequently, one set of the sample was stored in the iron pipe device to shield from environmental magnetic field; whereas the other set of the sample was exposed to environmental magnetic field. The solvent shell relative intensities of the samples were measured over a period of time following the storage at different temperatures. Table 1 and FIG. 1 summarize the relative NOE measurements from magnetic field shielded sample.

TABLE 1

(Magnetic Field Shielded)

| Steps | Sample Condition Toluene Conc.: 0.8M, Water Content: 0.1M | Solvent Shell Relative Intensity (Ratio of NOE) |
|---|---|---|
| 1 | Room temperature (RT, 23-24° C.) start | 2.65 |
| 2 | 22 hours after storage in iron pipe device at RT | 2.69 |
| 3 | Another 22 hours exposed to environmental magnetic field, and then warmed up to 35° C. | 2.37 |
| 4 | Another 22 hours after storage in iron pipe device (RT) | 2.39 |
| 5 | Another 22 hours exposed to environmental magnetic field (RT) | 2.38 |
| 6 | Another 22 hours exposed to environmental magnetic field (RT) | 2.54 |
| 7 | Another 22 hours exposed to environmental magnetic field (RT) | 2.68 |
| 8 | Another 22 hours exposed to environmental magnetic field (RT) | 2.71 |
| 9 | Warmed up to 45° C. | 2.69 |
| 10 | Another 22 hours of storage in iron pipe device (RT) | 2.70 |
| 11 | Another 22 hours exposed to environmental magnetic field, and then warmed up to 55° C. | 2.69 |
| 12 | Another 22 hours exposed to environmental magnetic field at RT | 2.66 |
| 13 | Warmed up to 55° C. | 2.68 |
| 14 | Another 22 hours of storage in iron pipe device (RT) | 2.73 |
| 15 | Another 22 hours exposed to environmental magnetic field, and then warmed up to 55° C. | 2.69 |
| 16 | Another 22 hours exposed to environmental magnetic field at RT | 2.71 |

Figure 2:
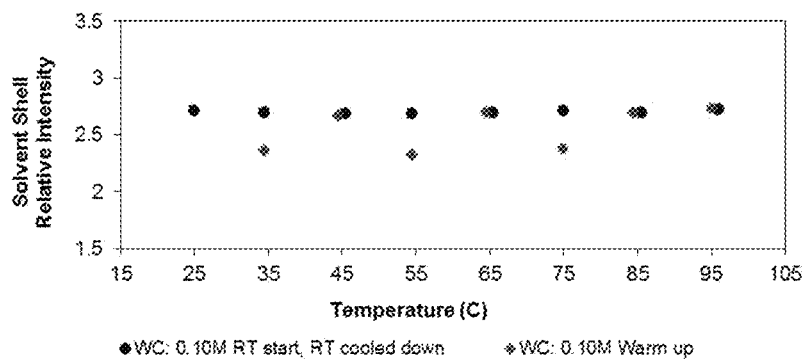
FIG. 2 demonstrates the results of the measurement of relative NOE intensities of the sample exposed to surrounding magnetic field. The plot is for the solvent shell relative NOE intensity vs. temperature. In this study, the solvent was 50% DMSO-50% DMSO-d6, the toluene concentration was 0.8 M, and water concentration was 0.10 M.

Table 2 and FIG. 2 detail the measurements of relative NOE intensities from the sample exposed to surrounding magnetic field.

TABLE 2

(Exposed to environmental magnetic field)

| Steps | Sample Condition Toluene Conc.: 0.8M, Water Content: 0.1M | Solvent Shell Relative Intensity (Ratio of NOE) |
|---|---|---|
| 1 | Room temperature (RT, 23-24° C.) start | 2.71 |
| 2 | 22 hours after storage in iron pipe device at RT | 2.69 |
| 3 | Another 22 hours exposed to environmental magnetic field, and then warmed up to 35° C. | 2.36 |
| 4 | 22 hours RT cooled down and exposed to environmental magnetic field | 2.70 |
| 5 | Warmed up to 45° C. | 2.67 |
| 6 | 22 hours RT cooled down and exposed to environmental magnetic field | 2.69 |
| 7 | Warmed up to 55° C. | 2.32 |
| 8 | 22 hours RT cooled down and exposed to environmental magnetic field | 2.69 |
| 9 | Warmed up to 65° C. | 2.70 |
| 10 | 22 hours RT cooled down and exposed to environmental magnetic field | 2.70 |
| 11 | Warmed up to 75° C. | 2.38 |
| 12 | 22 hours RT cooled down and exposed to environmental magnetic field | 2.71 |
| 13 | Warmed up to 85° C. | 2.70 |
| 14 | 22 hours RT cooled down and exposed to environmental magnetic field | 2.70 |
| 15 | Warmed up to 95° C. | 2.73 |
| 16 | 22 hours RT cooled down and exposed to environmental magnetic field | 2.72 |

As demonstrated above, the original solvent shell relative intensity of the sample exposed to environmental magnetic field recovered its original intensity within 24 hours. In contrast, the recovery period for the sample stored in the iron pipe device after being warmed up at 35° C. was much longer, about 72 hours, to recover the original solvent shell relative intensity, shown in Table 3 below.

TABLE 3

Solvent Shell Relative NOE Intensity over Time

| Storage Condition | 0 hour | After 22 hours in iron pipe device | 24 hours | 48 hours | 72 hours |
|---|---|---|---|---|---|
| Stored in iron pipe device | 2.37 | 2.39 | 2.38 | 2.54 | 2.68 |

Additionally, for the sample exposed to environmental magnetic field, the Toluene-DMSO system reached thermodynamic equilibrium at 85-95° C. In contrast, for the magnetic field shielded sample, the Toluene-DMSO system reached thermodynamic equilibrium at a much lower temperature, 55° C.

This study demonstrates that environmental magnetic filed affects the molecular dipole interaction in solutions, which can be detected by the delay of solvent shell NOE intensity recovery from its "activation intensity" to its "equilibrium/original intensity", and by decreasing the system thermodynamic equilibrium temperature.

1.2 DMSO 1H $(T1)_M$ Relaxation Study

The DMSO 1H $(T1)_M$ Relaxation Study was performed similar to the NOE study described in section 1.1 above. Instead of measuring NOE intensity, the DMSO 1H $(T1)_M$ relaxation time was measured in this study. The NMR parameters used in DMSO 1H T1 and $(T1)_M$ experiments were: D1[s]=30, TD=10, DS=2, AQ[s]=0.9893436 and NS=8. The sample preparation and T1 measurements followed the heating/cooling steps and procedures as performed in the NOE studies. The T1 and $(T1)_M$ relaxation data presented herewith were the average of six T1 measurements and verified by another set of independent experiments with a new sample to ensure data reproducibility.

Specifically, a 0.8 M Toluene-50% DMSO-50% DMSO-d6 solution with water content of 0.10 M was subjected to different decrease and recovery activation temperature stages and an "equilibrium temperature" of 85° C.-95° C.

Figure 3:
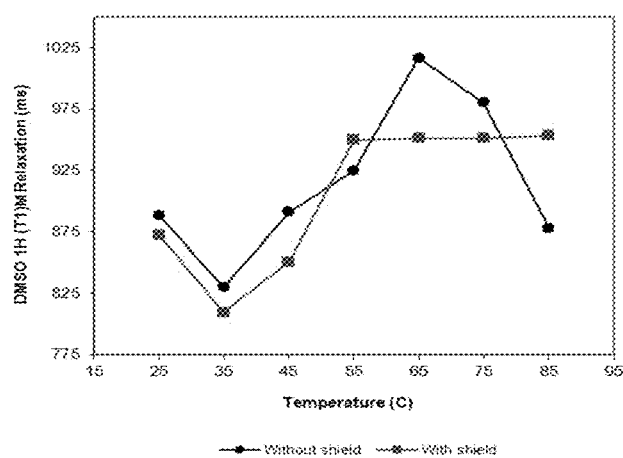
FIG. 3 is a joined plot of DMSO 1H $(T1)_M$ relaxation with surrounding magnetic field shielded (square) and without surrounding magnetic field shielded in (circle) vs. temperature.

Results: The DMSO 1H $(T1)_M$ relaxation dropped to the lowest point at the first cycle of warming up to 35° C. and cooling down. However, when the sample was warmed to 35° C. again, and then left in iron pipe device for 20 hours, the DMSO 1H $(T1)_M$ relaxation did not return to the lowest level. This observation was consistent with the NOE study result. Subsequently, when the sample was out of iron pipe device, the sample was subjected to further warming up and cooling down cycles at 45° C., 55° C., 65° C., 75° C. and 85° C., respectively. After the sample was warmed up in 55° C. water bath for 6 min, the sample reached "equilibrium" within the studied temperature range from room temperature to 85° C. This observation was also consistent with the NOE study. The results are summarized in FIG. 3.

In sharp contrast, the sample which was subjected to the initial cycle of heating to 35° C. and cooling and exposed to environmental magnetic field continued increasing to the highest relaxation time following the warming up to 55° C.

This study demonstrates that the DMSO 1H $(T1)_M$ relaxation of the sample exposed to environmental magnetic field is different from that of the sample shielded from environmental magnetic field, indicating that environmental magnetic field has an impact on dipole molecular interaction and the formation of DMSO-Toluene molecular assembly, which is consistent with the results from NOE study.

EXAMPLE 2

Effect of Environmental Magnetic Field on Cell Growth Under Normal Growth Condition This example demonstrates the effect of environmental magnetic field on in vitro cell growth at 37° C.

Materials and Device: The growth of non-small cell lung cancer cell line was investigated while being exposed to environmental magnetic field or being shielded from environmental magnetic field. The cell line was divided into three equal portions. The first sample was cultured in a surrounding magnetic shielded box (an iron shielding box), which was made from galvanized iron and copper, including the cover. The structure of the box allowed natural air flow of the incubator, which air contained 5% of carbon dioxide. The second sample was cultured in a plastic box, the structure of which was the same as the iron shielding box. The third sample was cultured in the absence of any surrounding box.

All three samples were incubated simultaneously in the same incubator at same time and following the same standard cell culture procedure. The temperature of incubator was maintained at 37° C.

Figure 4:
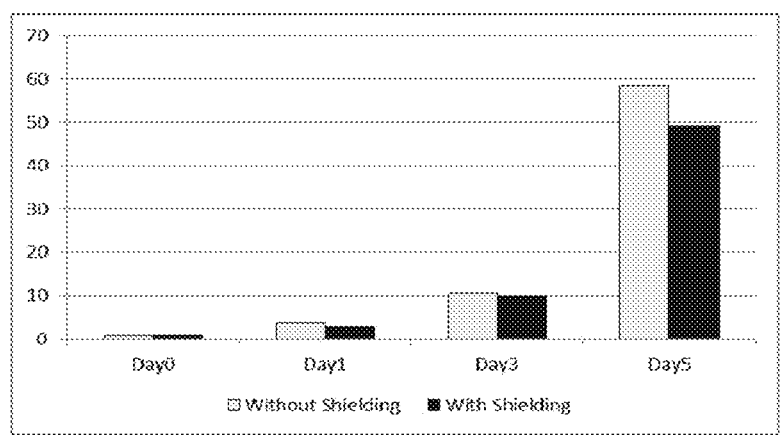
FIG. 4 compares the in vitro growth of non-small cell lung cancer cells in an iron shielding box (with shielding) and in a plastic box (without shielding), respectively.

Results: After incubation for 5 days, the population of the non-small cell lung cancer cells cultured in the iron shielding box decreased in comparison to the control cultured in a plastic box at each time point, as shown in FIG. 4. However, the population of the cells cultured in the plastic box was about the same as the population of the cells cultured in the absence of any surrounding box. The experiment was repeated to ensure reproducibility.

This example demonstrates that shielding of the environmental magnetic field has an impact on the cell growth in vitro.

EXAMPLE 3

Effect of Environmental Magnetic Field on Cell Growth Under Normal Growth Condition This example demonstrates the effect of environmental magnetic field on cell growth in vitro at 37° C.

Materials and Methods

Materials and Instruments

Non-small cell lung cancer cells (A549) and breast cancer cells (MCF-7) were provided by the Cell Resource Center, Shanghai Institute of Life Sciences, Chinese Academy of Sciences). Other materials used were as follows: RPMI 1640 medium (R-6504-1L, SIGMA-ALDRICH Corp); Trypsin (T4424-100 ml, SIGMA-ALDRICH Corp); Fetal Bovine Serum (FBS) (500 ml, Gibco Laboratories, Grand Island, N.Y.); Penicillin and Streptomycin (100 ml, Lonza Walkersville Inc.); Taxol (Paclitaxel, T7191-5 mg, SIGMA-ALDRICH Corp); Cell Counting Kit-8 (DOJINDO); Microplate Reader RT-6000 (Rayto Life and Analytical Sciences Co., Ltd); Constant Temperature Water Bath (Fisher Scientific).

Magnetic Field Shielding Device

The surrounding magnetic field shielding device and the plastic box used in this experiment were the same as those described in Example 2 above.

Cell Culture

The human non-small cell lung cancer cells (A549) and human breast cancer cell (MCF-7) were supplied by the Cell Resource Center, Shanghai Institute of Life Sciences. The cells were maintained in a monolayer and were grown at 37° C. in an atmosphere of 5% $CO_2$ with moisture in RPMI 1640 medium, supplemented with 10% fetal bovine serum. The medium also contained 100 U/L Penicillin and 100 mg/L Streptomycin. The cells at exponentially growing phase were used in the experiments.

Culture of Taxol Resistant Cell Line A549-T24

The protocol described by Kavallaris et al., *J. Clin. Invest.*, 100(5): 1282-1293 (1997)[13] was followed to culture taxol-resistant human lung carcinoma cells A549. The human non-small cell lung cancer cells A549 were maintained in RPMI 1640 containing 10% FBS and 1% Penicillin-Streptomycin. For inducing its resistance to Taxol, in a stepwise manner, Taxol was added into the culture medium with periodically increasing its concentration. A549 cells were initially exposed to 3 nM of Taxol, and once normal growth was achieved, cells were maintained at this concentration. In two weeks, the Taxol dose was increased by two-fold, such as 3 nM, 6 nM, 12 nM, until the final drug concentration of 24 nM was achieved to develop Taxol-resistant cells. The obtained cells were maintained at a Taxol concentration of 24 nM. These Taxol-resistant cells were named as A549-T24.

Experimental Methods

The human non-small cell lung cancer cells (A549) or the human breast cancer cells (MCF-7) were grown in 96 well plates. The growth of non-small cell lung cancer cell line and the breast cancer cell line were investigated while being exposed to environmental magnetic field or being shielded from environmental magnetic field. Each cell culture was separated into three equal portions. The first sample was cultured in a surrounding magnetic field shielded box (an iron shielding box). The second sample was cultured in a plastic box, and the third sample was cultured in the absence of any surrounding box as a control. All of the samples were placed in the incubator with an atmosphere containing 5% $CO_2$ and at a temperature of 37° C. The cell growth rates were examined periodically by harvesting the cells and determining cell viability using the cell counting kit-8 and microplate reader RT-6000. The experiments were continued for four to seven days depending on the cell types and the respective growth rates.

The Determination of Cell Viability

Cell count kit-8 (CCK-8) (a microplate reader manufactured by Dojindo Molecular Technologies, Inc.) allows sensitive colorimetric assays for the determination of cell viability. CCK-8 was used to determine the cell counts and the standard protocol recommended by the manufacturer was followed to measure the absorbency of living cells at 450 nm to determine the cell viability and the cell growth rate under the influence of shielding magnetic field, and without shielding of magnetic field to study the effect of environment magnetic field on cell growth.

Heating Procedure

The water bath cell heating procedure was described in detail by Alfieri et al., Cancer Research 41: 1301-1305 (1981); and Herman et al., Cancer Research 41: 3519-1523 (1981)[14, 15]. Specifically, exponentially growing A549 cells or MCF-7 cells were diffused, separated and suspended in cell culture medium in a centrifugal tube, and then the tube was immersed in a constant temperature water bath (39° C.±0.02° C.). A thermometer was placed in the culture medium of the tube. When the temperature of the internal culture medium reached 39° C., the heating time started to count and the heating would last for 20 minutes.

Statistical Analysis

Data were tested for statistical significance using "The normality plot to check whether the data are from a normal distribution population, and a t-test to infer two means is same or significantly different"[16, 17].

Results

A. Effect of Environmental Magnetic Field on In Vitro Growth of Non-Small Cell Lung Cancer Cells A549 at 37° C.

Figure 5:
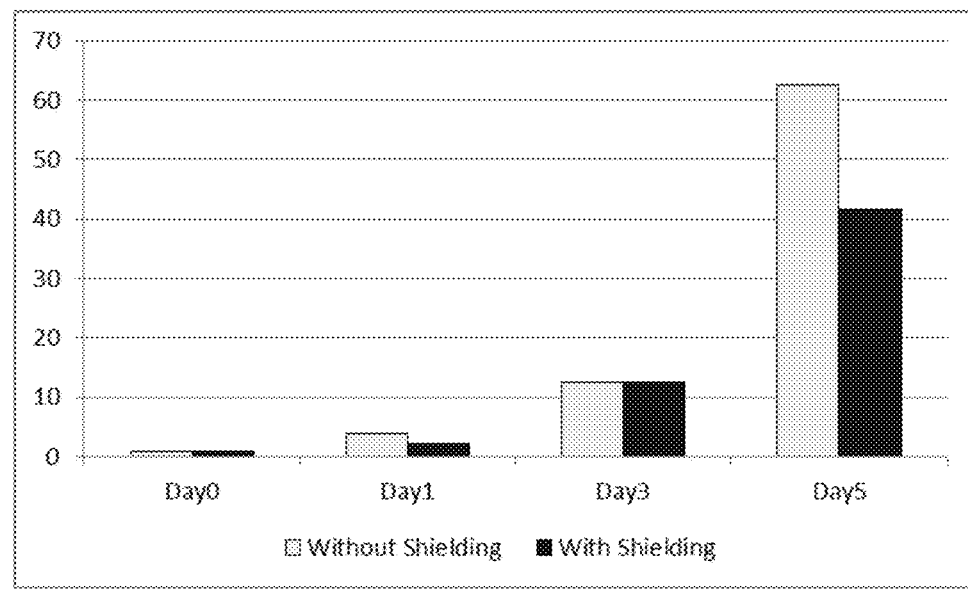
FIG. 5 compares the in vitro growth of non-small cell lung cancer cells A549 in an iron shielding box (with shielding) and in a plastic box (without shielding), respectively.

After incubation for 5 days, the population of the non-small cell lung cancer cells cultured in the iron shielding box decreased by 33.3% (A549, Day 5, P<0.0005, Std≤5%) in comparison to the control cultured in a plastic box at each time point, as shown in FIG. 5. However, the population of the cells cultured in the plastic box was about the same as the population of the cells cultured in the absence of any surrounding box. The results were the average of 7 experimental results and the experiments were repeated to ensure reproducibility.

This experiment demonstrates that shielding of the environmental magnetic field has an impact on the cell growth in vitro.

Figure 6:
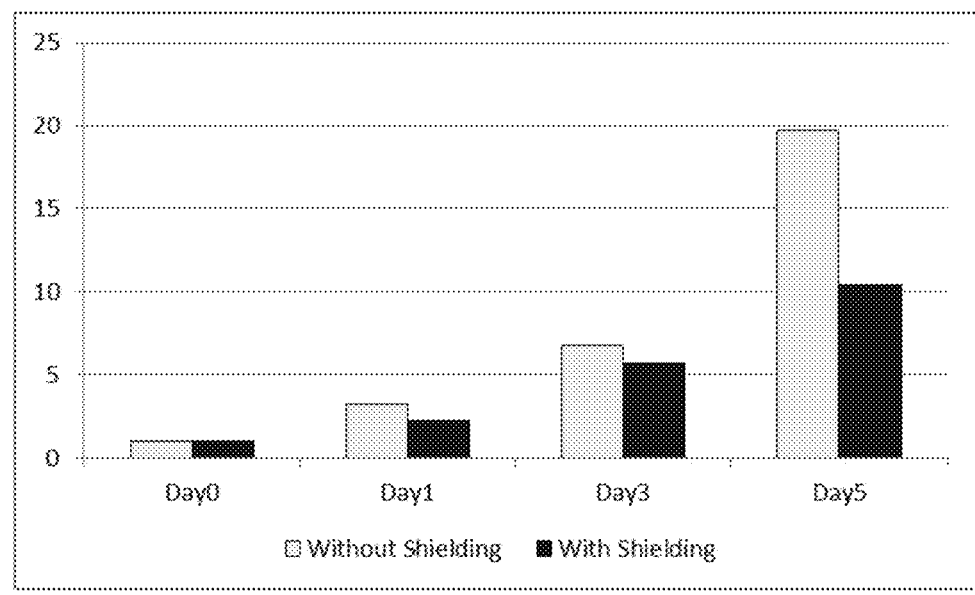
FIG. 6 compares the in vitro growth of non-small cell lung cancer cells A549 in the presence of Taxol in an iron shielding box (with shielding) and in a plastic box (without shielding), respectively.

B. Effect of Environmental Magnetic Field on In Vitro Growth of Non-Small Cell Lung Cancer Cell A549 at 37° C. in the Presence of Taxol The non-small cell lung cancer cell A549 was cultured and incubated in a medium, which contained 5 nM Taxol, at 37° C. After 3 days of incubation, the growth of A549 in the iron shielding box was 16.3% slower (P<0.001, Std≤5%) than the control cell growth cultured in a plastic box; after 5 days of incubation, the growth of the A549 cells in the iron shielding box decreased by 47.3% (P<0.0005, Std≤5%) in comparison to the control cultured in a plastic box as shown in FIG. 6. This result indicates that the 5 nM concentration of Taxol is close to the IC50 (IC50: the drug concentration, at which the cell growth is suppressed to 50%). As reported by Georgiadis et al., Clinical Cancer Research, 3: 449-454, (1997)[18], the IC50 for the most sensitive non-small lung cancer cell to Taxol is 0.0099 µM. Thus, under the condition of shielding of environmental magnetic field, the efficacy of Taxol at least was doubled. The results were the average of 7 experimental results and the experiments were repeated to ensure reproducibility.

Figure 7:
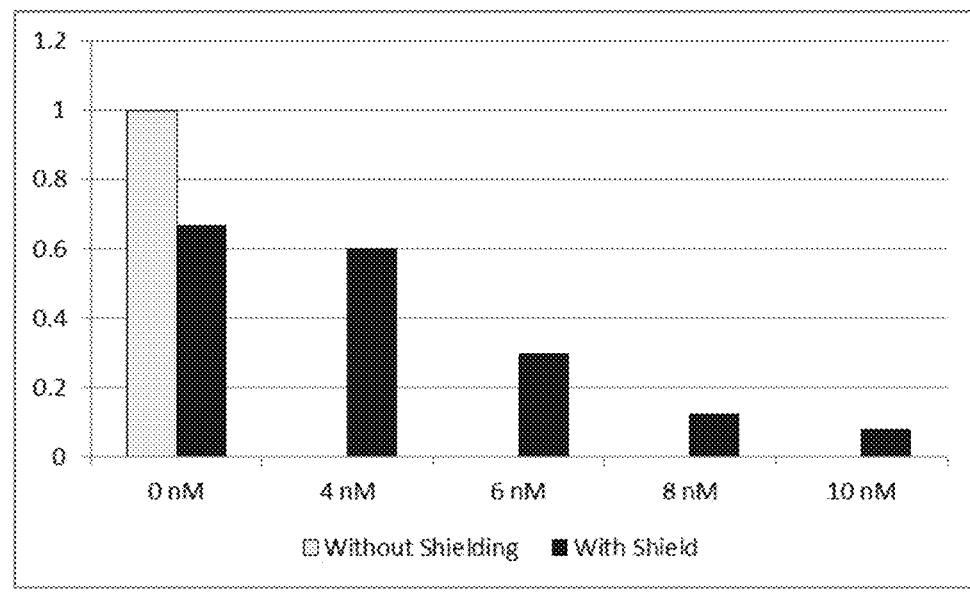
FIG. 7 compares the in vitro growth of non-small cell lung cancer cells A549 in the presence of various of concentrations of Taxol in an iron shielding box (with shielding) and in a plastic box (without shielding), respectively.

For evaluation of IC50 of Taxol under the effect of shielding surrounding magnetic field, the above experiments were repeated at different Taxol concentration. The results are summarized in FIG. 7.

This experiment shows that the shielding of the environmental magnetic field combined with an anti-tumor agent dramatically increases the efficacy of the agent towards the tumor in vitro.

C. Effect of Environmental Magnetic Field on the In Vitro Growth of Drug-Resistant Non-Small Cell Lung Cancer Cells Growth A549-T24 at 37° C.

The Taxol-resistant non-small cell lung cancer cells A549-T24 were cultured, and then used in the study of the effect of environmental magnetic field on non-small cell lung cancer cells growth in vitro at 37° C. The experimental methods are described as above.

(1) Effect of Environmental Magnetic Field on the In Vitro Growth of Taxol-Resistant Non-Small Cell Lung Cancer Cells A549-T24 at 37° C.

Figure 8:
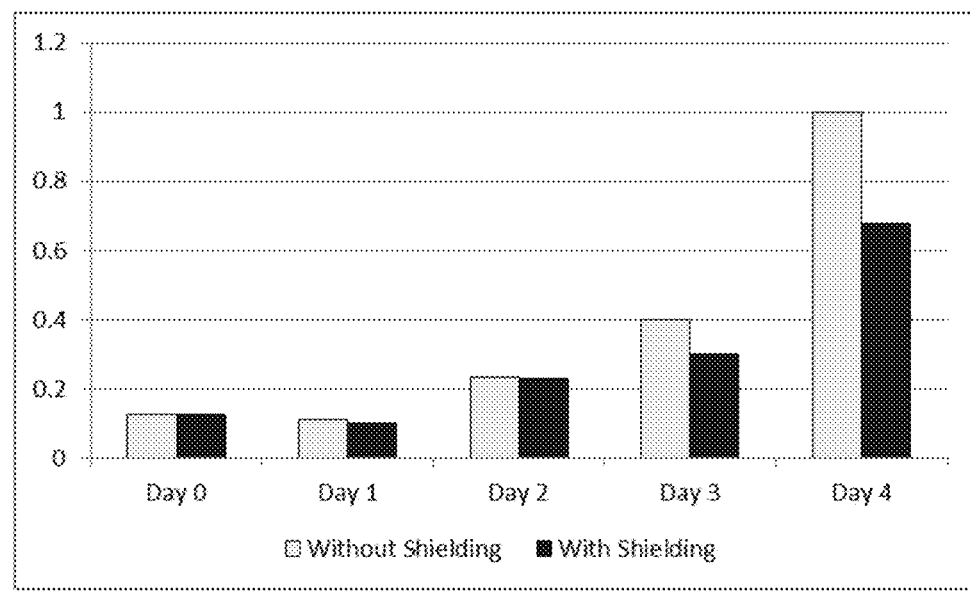
FIG. 8 compares the in vitro growth of Taxol-resistant non-small cell lung cancer cells A549-T24 in an iron shielding box (with shielding) and in a plastic box (without shielding), respectively.

After incubation for 3 days or 4 days, the population of A549-T24 cultured in the iron shielding box decreased by 25.0% (day 3, P<0.01, Std≤5%) or by 32.4% (day 4, P<0.0005, Std≤5%) in comparison to the control cultured in a plastic box at each time point, as shown in FIG. 8. These results were consistent with the results obtained from the A549 cells. The data were the average of 12 experimental results and the experiments were repeated to ensure reproducibility.

This experiment indicates that shielding of the environmental magnetic field also has an impact on the in vitro growth of drug-resistant cells.

Figure 9:
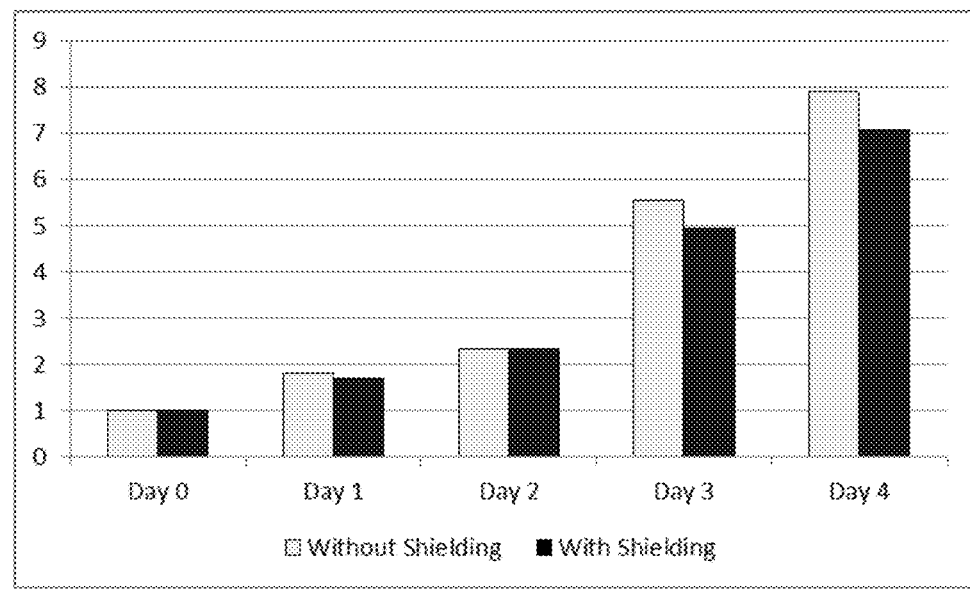
FIG. 9 compares the in vitro growth of Taxol-resistant non-small cell lung cancer cells A549-T24 in the presence of Taxol in an iron shielding box (with shielding) and in a plastic box (without shielding), respectively.
Figure 10:
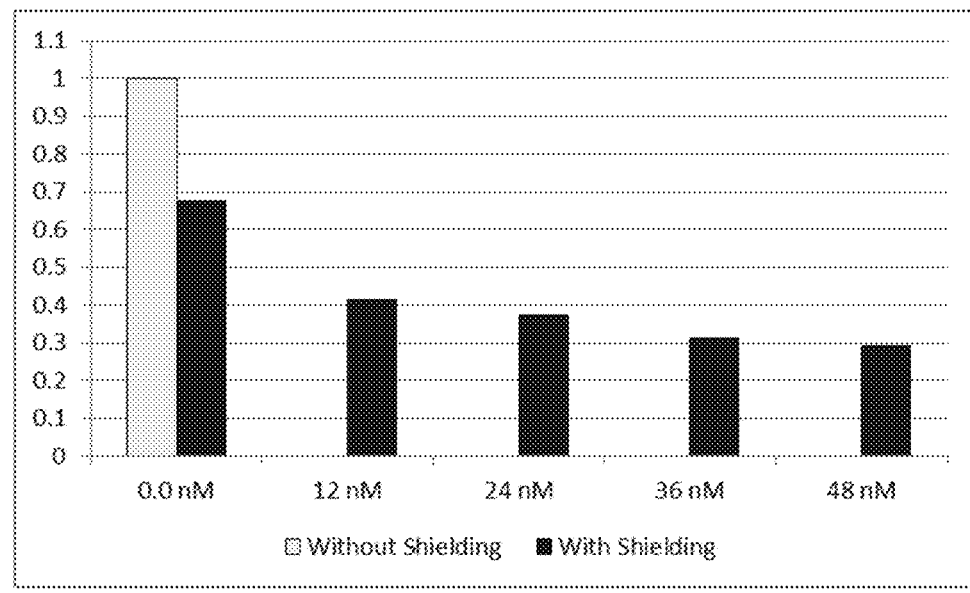
FIG. 10 compares the in vitro growth of Taxol-resistant non-small cell lung cancer cells A549-T24 in the presence of various concentrations of Taxol in an iron shielding box (with shielding) and in a plastic box (without shielding), respectively.

(2) Effect of Environmental Magnetic Field on the In Vitro Growth of Taxol-Resistant Non-Small Cell Lung Cancer Cells A549-T24 at 37° C. in the Presence of 12 nM Taxol The Taxol-resistant non-small cell lung cancer cells A549-T24 were cultured and incubated in a medium, which contained 12 nM Taxol, at 37° C. After 3 days or 4 days of incubation, the growth of A549-T24 in the iron shielding box was 11.2% (day 3, P<0.01, Std≤5%) or 10.7% (day 4, P<0.001, Std≤5%) slower than the control A549-T24 cell growth cultured in a plastic box as shown in FIG. 9. The results were the average of 7 experimental results and the experiments were repeated to ensure reproducibility To evaluate the efficacy of Taxol at different concentrations and to determine the IC50 for A549-T24 cells under the effect of shielding surrounding magnetic field, the experiment described above was conducted at different Taxol concentrations. FIG. 10 summarizes the day 4 results at different Taxol concentrations for A549-T24 Taxol-resistant non-small cell lung cancer cells.

Under the condition of shielding surrounding magnetic field, Taxol was able to suppress the growth of Taxol-resistant non-small cell lung cancer cells efficiently. The IC50 to Taxol for the Taxol-resistant non-small cell lung cancer cells was about 10 nM (≤12 nM).

EXAMPLE 4

Effect of Environmental Magnetic Field on Cell Growth Following Heat Shock

This example demonstrates the effect of environmental magnetic field on in vitro cell growth at 37° C. following a heat shock at 39° C.

The non-small cell lung cancer cell cultures were subjected to a heat shock to 39° C. for 30 minutes, then incubated at 37° C. for 48 hours under the same conditions described in Example 2 above.

Results: After incubation at 37° C. for 48 hours, the population of the cells cultured in the iron shielding box did not change significantly in comparison to the starting point. However, the population of the cells cultured in the plastic box decreased in comparison to the starting point, indicating gradual cell death resulting from progressive cell injury post heat shock.

This example demonstrates that shielding of the environmental magnetic field has an effect on prolonging the survival of injured cells in vitro.

EXAMPLE 5

Effect of Environmental Magnetic Field on Cell Growth Following Heat Shock

This example demonstrates the effect of environmental magnetic field on in vitro cell growth at 37° C. following a heat shock at 39° C.
Heating Procedure The heating procedure was the same as that described in Example 3 above. When the experiments were conducted in agar, the heating time was 30 minutes.
Materials and Methods The materials and methods were the same as those disclosed in Example 3 above.
Results
A. Cell Injury Due to Heat Shock The non-small cell lung cancer cell A549 cultures were subjected to a heat shock at 39° C. for 20 minutes. Subsequently, the cells were incubated at 37° C. for 6 days in the absence of any shielding boxes. An un-heated A549 cultures were also incubated simultaneously at 37° C. as a control.

Figure 11:
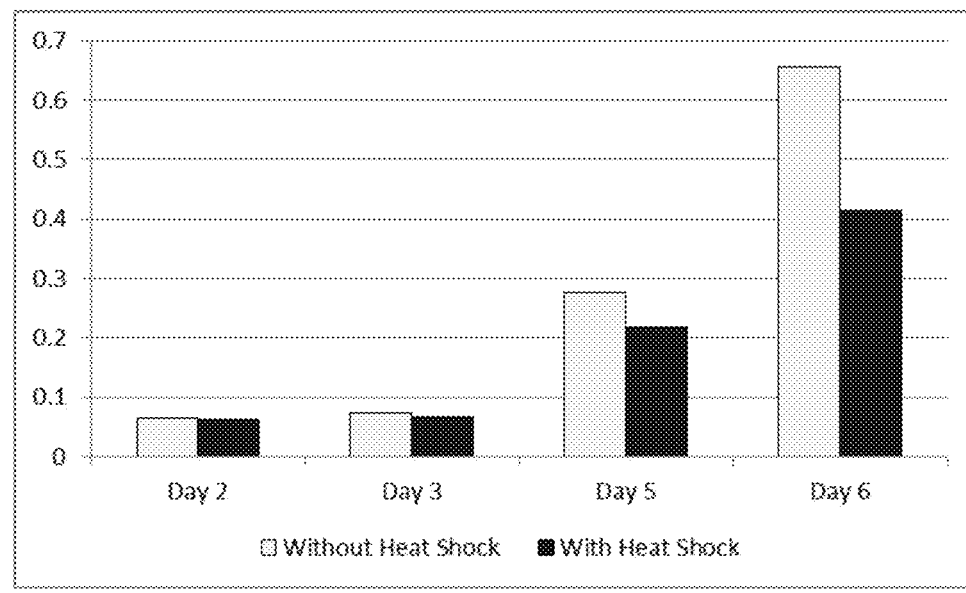
FIG. 11 shows progressive cell death of non-small cell lung cancer cells A549 due to heat shock at 39° C.

Due to progressive cell injury post-heat shock, the growth of A549 cells subjected to heat shock was reduced by 21.1% ($P<0.15$) on day 5 and by 36.7% ($P<0.0005$) on day 6 comparing to unheated cells (control). The results were the average of 6 experiments, and summarized in FIG. 11. The experiments were repeated to ensure reproducibility.
B. Effect of Environmental Magnetic Field on Cell Growth after Heat Shock When the experiments were performed in agar, after heat shock, A549 non-small cell lung cancer cells were incubated at 37° C. for 48 hours. The population of the cells cultured in the iron shielding box did not change significantly in comparison to the population of the cells at the starting point. However, the population of the cells cultured in the plastic box decreased in comparison to the starting point, indicating that gradual cell death resulted from progressive cell injury post heat shock, and that heat shock changed the molecular orientation and interactions in the cell due to the molecule thermal motion.

Figure 12:
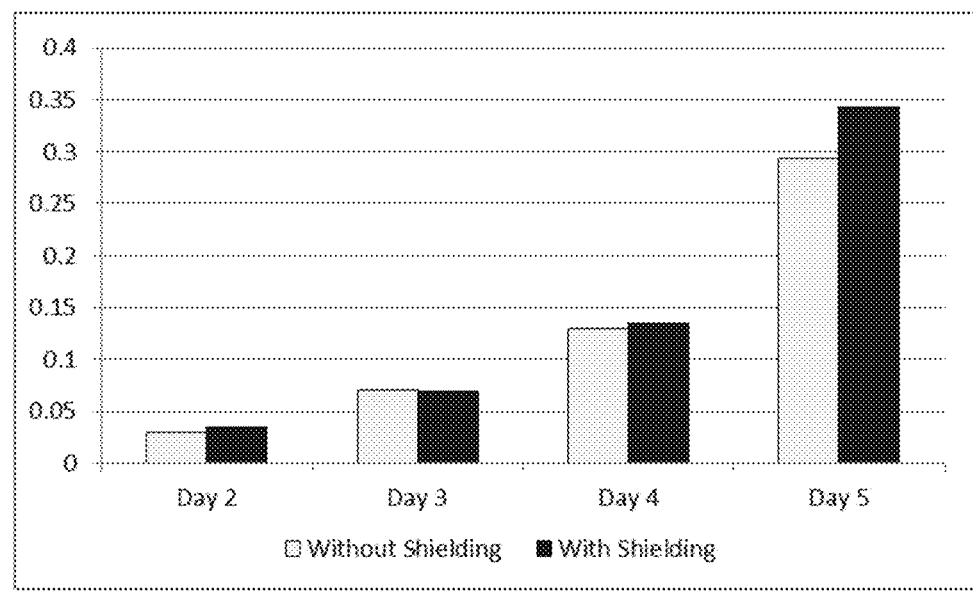
FIG. 12 compares the in vitro growth of non-small cell lung cancer cells A549 post-heat shock in an iron shielding box (with shielding) and in a plastic box (without shielding), respectively.

As shown in FIG. 12, the cell growth on day 5 in the plastic box was 17.1% ($P<0.01$) slower in comparison to the cell growth in the iron shielded box. The results were the average of 12 experiments, and the experiments were repeated to ensure reproducibility.

This experiment demonstrates that shielding of the environmental magnetic field has an effect on prolonging the survival of injured cells in vitro, and that changing molecular interaction in cells induces the change of the effect of surrounding magnetic field on cells.

EXAMPLE 6

Figure 13:
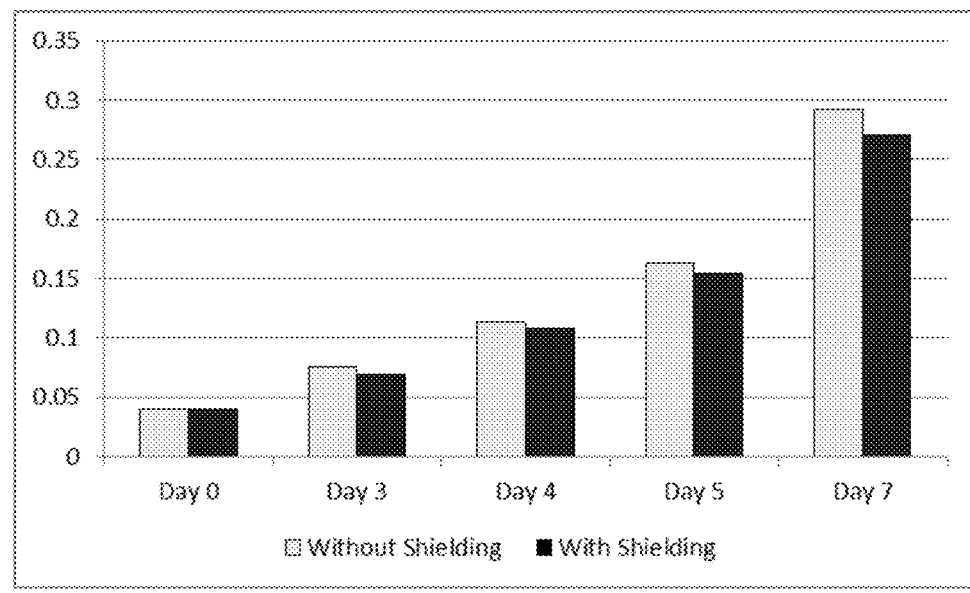
FIG. 13 compares the in vitro growth of breast cancer cells MCF-7 in an iron shielding box (with shielding) and in a plastic box (without shielding), respectively.
Figure 14:
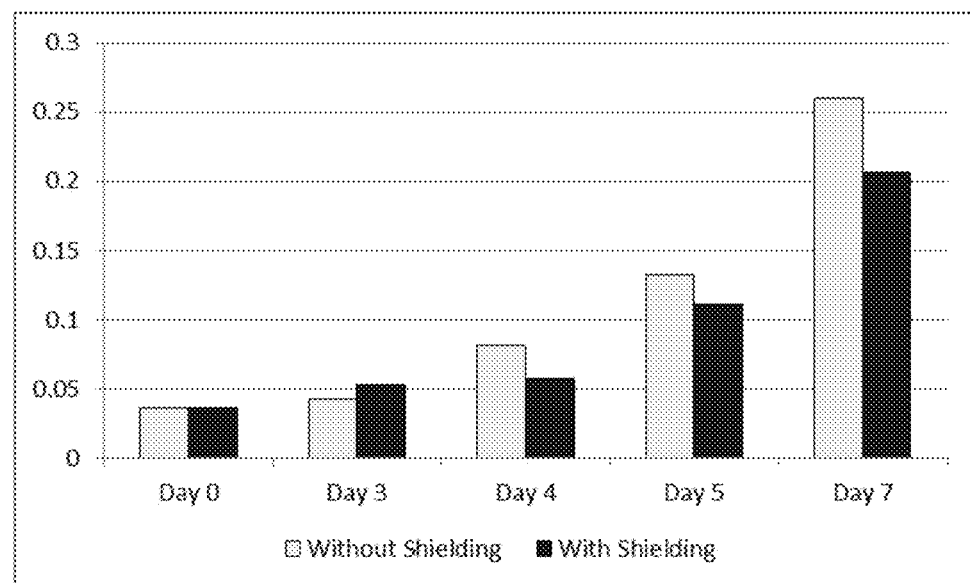
FIG. 14 compares the in vitro growth of breast cancer cells MCF-7 post-heat shock in an iron shielding box (with shielding) and in a plastic box (without shielding), respectively.

Effect of Environment Magnetic Field on Breast Cancer Cell MCF-7 Growth Under Normal Growth Condition and Following Heat Shock A. The Effect of Environmental Magnetic Field on MCF-7 Cell Growth In Vitro at 37° C. (Under Cell Normal Growth Condition).
Materials and Methods The materials and methods were the same as those disclosed in Example 3 above.
Results After incubation for 7 days in the cell culture medium, which was changed on day 3 and day 5, the growth of the breast cancer cells MCF-7 cultured in the iron shielding box was decreased by 5.5% on day 5 and by 7.4% on day 7. The growth of the cells cultured in the plastic box was about the same as the growth of the cells cultured in the absence of any surrounding box. The results were the average of 6 experimental results and the experiments were repeated to ensure reproducibility. The results are demonstrated in FIG. 13. The shielding of the environmental magnetic field appeared to have no significant effect on the in vitro growth of breast cancer cell MCF-7.
B. Effect of Environmental Magnetic Field on the In Vitro Growth of Breast Cancer Cells MCF-7 at 37° C. Following a Heat Shock at 39° C.
Heating Procedure The heating procedure was the same as that described in Example 3 above.
Materials and Methods The materials and methods were the same as those disclosed in Example 3 above.
Results After the heat shock, the breast cancer cells MCF-7 were incubated for 7 days in the cell culture medium, which was changed on day 3 and day 5. The growth of the breast cancer cells (MCF-7) cultured in the iron shielding box decreased by 16.5% on day 5 (MCF-7, Day 5, $P<0.0005$) and by 20.7% on day 7 (MCF-7, Day 7, $P<0.0005$) in comparison to the control cultured in a plastic box at each time point as shown in FIG. 14. The results were the average of 5 experimental results and the experiments were repeated to ensure reproducibility.

This experiment demonstrates that shielding of the environmental magnetic field has a significant effect on the in vitro growth of breast cancer cells MCF-7 after heat shock.

CITED REFERENCES

All cited references are incorporated by reference in their entireties.
1. Jordan et al., "Microtubules and actin filaments: dynamic targets for cancer chemotherapy," *Current Opinion in Cell Biology*, 10: 123-130 (1998).

2. Jordan et al., "Microtubules as a target for anticancer drugs," *Nat. Rev. Cancer,* 4: 253-265 (2004).

3. Schiff et al., "Taxol stabilizes microtubules in mouse fibroblast cells," *Proc. Natl. Acad. Sci. USA,* 77: 1561-1565 (1980).

4. Yvon et al., "Taxol suppresses dynamics of individual microtubules in living human tumor cells," *Molecular Biology of the Cell,* 10: 947-959 (1999).

5. Lingderstrom-Lang et al., Lane Medical Lectures, vol. 6: 53, Standford University Press (1952).

6. Lumry et al., "The conformation changes of proteins," *J. Phys. Chem.* 58: 110 (1954).

7. Kauzmann, The mechanism of enzyme action, P 70, Johns Hopkins Press, (1954).

8. Dill, "Dominant forces in protein folding," *Biochemistry,* 29: 7133-7155 (1990).

9. Debye, "Light scattering in soap solutions," *Ann. N.Y. Acad. Sci.* 51: 575 (1949).

10. Michl, "Special issue on van der Waals clusters II," *Chem. Rev.,* 94: 1721-2160 (1994).

11. Klein, "Cancer. The metastasis cascade," *Science* 321 (5897): 1785-7 (2008).

12. Chiang et al., "Molecular basis of metastasis," *The New England Journal of Medicine* 359 (26): 2814-23 (2008).

13. Kavallaris et al., *J. Clin. Invest.,* 100(5): 1282-1293 (1997);

14. Alfieri et al., *Cancer Research* 41: 1301-1305 (1981);

15. Herman et al., *Cancer Research* 41: 3519-1523 (1981);

16. J. A. Rice, *Mathematical Statistics and Data Analysis,* 3$^{rd}$. ed., Duxbury Advanced (2006);

17. D. S. Yates, D. S. Moore, D. S. Starnes, *The Practice of Statistics,* W.H. Freeman and Company" (2003); and 18. Georgiadis et al., *Clinical Cancer Research,* 3: 449-454, (1997).

What is claimed is:

1. A portable, therapeutic device for mammalian therapy, the device comprising:
a housing consisting of and formed entirely by an inner layer of copper and an outer layer of iron positioned directly in contact with an entire outer surface of the inner layer of copper, an entire outer surface of the outer layer of iron being an outer surface of the device, the housing configured to surround at least a portion of a mammalian body, wherein the device is capable of producing an artificial, stabilized magnetic field which is the same as a reference stabilized magnetic field produced by nuclear magnetic resonance (NMR), and being capable of shielding at least a portion of the mammalian body from environmental magnetic fields,
wherein the device is sized and configured to be attached to or implanted into the mammalian body, and
wherein the portable device permits the mammalian body to experience the artificial stabilized magnetic field for a therapeutically effective time at a therapeutically effective magnetic field strength to result in altered dipolar interactions of molecules in a cell so as to alter cellular physiology of the cell.

2. The device of claim 1, wherein the device is a body wrap.

3. The device of claim 1, wherein the device is a jumper suit.

4. The device of claim 1, wherein the device is a glove.

5. The device of claim 1, wherein the device is a sock.

* * * * *